(12) United States Patent
Dietz et al.

(10) Patent No.: US 8,080,064 B2
(45) Date of Patent: Dec. 20, 2011

(54) TIBIAL TRAY ASSEMBLY HAVING A WIRELESS COMMUNICATION DEVICE

(75) Inventors: Terry L. Dietz, Columbia City, IN (US); Edward J. Caylor, III, Fort Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 560 days.

(21) Appl. No.: 11/771,459

(22) Filed: Jun. 29, 2007

(65) Prior Publication Data
US 2009/0005876 A1 Jan. 1, 2009

(51) Int. Cl.
*A61F 2/38* (2006.01)
(52) U.S. Cl. ............... 623/20.32; 623/20.33; 623/20.34
(58) Field of Classification Search .... 623/20.32–21.19; A61F 2/38
See application file for complete search history.

(56) References Cited

U.S. PATENT DOCUMENTS

| | | |
|---|---|---|
| 4,352,960 A | 10/1982 | Dormer |
| 4,436,684 A | 3/1984 | White |
| 4,467,809 A | 8/1984 | Brighton |
| 4,549,547 A | 10/1985 | Brighton et al. |
| 4,830,021 A | 5/1989 | Thornton |
| 4,936,862 A | 6/1990 | Walker et al. |
| 5,193,539 A | 3/1993 | Schulman et al. |
| 5,197,488 A | 3/1993 | Kovacevic |
| 5,211,165 A | 5/1993 | Dumoulin et al. |
| 5,300,120 A | 4/1994 | Knapp et al. |
| 5,350,379 A | 9/1994 | Spievack |
| 5,356,411 A | 10/1994 | Spievack |
| 5,360,016 A | 11/1994 | Kovacevic |
| 5,362,996 A | 11/1994 | Yizraeli |
| 5,383,915 A | 1/1995 | Adams |
| 5,425,775 A | 6/1995 | Kovacevic et al. |
| 5,448,489 A | 9/1995 | Reuben |
| 5,469,862 A | 11/1995 | Kovacevic |
| 5,488,952 A | 2/1996 | Schoolman |
| 5,522,402 A | 6/1996 | Cooley |
| 5,523,746 A | 6/1996 | Gallagher |
| 5,536,269 A | 7/1996 | Spievack |
| 5,545,191 A | 8/1996 | Mann et al. |
| 5,610,966 A | 3/1997 | Martell et al. |
| 5,626,579 A | 5/1997 | Muschler et al. |
| 5,626,630 A | 5/1997 | Markowitz et al. |
| 5,662,111 A | 9/1997 | Cosman |

(Continued)

FOREIGN PATENT DOCUMENTS
EP 1172064 A2 1/2002
(Continued)

OTHER PUBLICATIONS

European Search Report for European Patent Application No. 08158868.3-1526, Dec. 4, 2008, 6 pgs.
(Continued)

*Primary Examiner* — Thomas J Sweet
*Assistant Examiner* — Jason-Dennis Stewart
(74) *Attorney, Agent, or Firm* — Barnes & Thornburg LLP

(57) ABSTRACT

A tibial tray assembly includes a platform having a stem extending downwardly from a bottom surface and a stem extension couple to the an end of the stem. The stem extension is electrically insulated from the stem. The tibial tray assembly also includes a wireless communication device configured to transmit data using the stem extension as an antenna.

18 Claims, 7 Drawing Sheets

U.S. PATENT DOCUMENTS

| | | |
|---|---|---|
| 5,704,939 A | 1/1998 | Justin |
| 5,715,837 A | 2/1998 | Chen |
| 5,741,215 A | 4/1998 | D'Urso |
| 5,741,316 A | 4/1998 | Chen et al. |
| 5,798,924 A | 8/1998 | Eufinger et al. |
| 5,807,258 A | 9/1998 | Cimochowski et al. |
| 5,832,488 A | 11/1998 | Eberhardt |
| 5,833,603 A | 11/1998 | Kovacs et al. |
| 5,855,609 A | 1/1999 | Knapp |
| 5,861,019 A | 1/1999 | Sun et al. |
| 5,961,553 A | 10/1999 | Coty et al. |
| 5,967,986 A | 10/1999 | Cimochowski et al. |
| 6,002,859 A | 12/1999 | Digioia, III et al. |
| 6,034,296 A | 3/2000 | Elvin et al. |
| 6,083,174 A | 7/2000 | Brehmeier-Flick et al. |
| 6,115,636 A | 9/2000 | Ryan |
| 6,126,690 A | 10/2000 | Ateshian et al. |
| 6,144,385 A | 11/2000 | Girard |
| 6,151,581 A | 11/2000 | Kraftson et al. |
| 6,161,080 A | 12/2000 | Aouni-Ateshian et al. |
| 6,169,925 B1 | 1/2001 | Villaseca et al. |
| 6,177,034 B1 | 1/2001 | Ferrone |
| 6,239,705 B1 | 5/2001 | Glen |
| 6,254,639 B1 | 7/2001 | Peckitt |
| 6,324,418 B1 | 11/2001 | Crowley et al. |
| 6,336,929 B1 | 1/2002 | Justin |
| 6,366,799 B1 | 4/2002 | Acker et al. |
| 6,369,694 B1 | 4/2002 | Mejia |
| 6,385,593 B2 | 5/2002 | Linberg |
| 6,400,272 B1 | 6/2002 | Holtzman |
| 6,442,432 B2 | 8/2002 | Lee |
| 6,447,448 B1 | 9/2002 | Ishikawa et al. |
| 6,456,256 B1 | 9/2002 | Amundson et al. |
| 6,458,161 B1 | 10/2002 | Gibbs et al. |
| 6,459,943 B1 | 10/2002 | Suetani et al. |
| 6,474,599 B1 | 11/2002 | Stomski |
| 6,480,745 B2 | 11/2002 | Nelson et al. |
| 6,529,127 B2 | 3/2003 | Townsend |
| 6,539,947 B2 | 4/2003 | Boies et al. |
| 6,559,620 B2 | 5/2003 | Zhou et al. |
| 6,565,576 B1 | 5/2003 | Stauch |
| 6,574,511 B2 | 6/2003 | Lee |
| 6,577,901 B2 | 6/2003 | Thompson |
| 6,628,989 B1 | 9/2003 | Penner et al. |
| 6,631,296 B1 | 10/2003 | Parramon et al. |
| 6,656,117 B2 | 12/2003 | Jentsch et al. |
| 6,656,135 B2 | 12/2003 | Zogbi et al. |
| 6,674,883 B1 | 1/2004 | Wei et al. |
| 6,687,131 B1 | 2/2004 | Miehling |
| 6,700,547 B2 | 3/2004 | Mejia et al. |
| 6,706,005 B2 | 3/2004 | Roy et al. |
| 6,708,065 B2 | 3/2004 | Von Arx et al. |
| 6,720,930 B2 | 4/2004 | Johnson et al. |
| 6,750,866 B1 | 6/2004 | Anderson, III |
| 6,772,002 B2 | 8/2004 | Schmidt et al. |
| 6,793,496 B2 | 9/2004 | Edic et al. |
| 6,799,066 B2 | 9/2004 | Steines et al. |
| 6,802,811 B1 | 10/2004 | Slepian |
| 6,804,558 B2 | 10/2004 | Haller et al. |
| 6,833,790 B2 | 12/2004 | Mejia et al. |
| 6,847,892 B2 | 1/2005 | Zhou et al. |
| 6,947,004 B2 | 9/2005 | Mejia et al. |
| 7,015,826 B1 | 3/2006 | Chan et al. |
| 7,047,076 B1 | 5/2006 | Li et al. |
| 7,191,007 B2 | 3/2007 | Desai |
| 7,191,013 B1 | 3/2007 | Miranda et al. |
| 7,218,232 B2 | 5/2007 | DiSilvestro et al. |
| 7,256,695 B2 | 8/2007 | Hamel et al. |
| 7,599,743 B2 | 10/2009 | Hassler, Jr. et al. |
| 7,599,744 B2 | 10/2009 | Giordano et al. |
| 2001/0051787 A1 | 12/2001 | Haller et al. |
| 2002/0013613 A1 | 1/2002 | Haller et al. |
| 2002/0013614 A1 | 1/2002 | Thompson |
| 2002/0024450 A1 | 2/2002 | Townsend et al. |
| 2002/0040234 A1 | 4/2002 | Linberg |
| 2002/0065539 A1 | 5/2002 | Von Arx et al. |
| 2002/0077562 A1 | 6/2002 | Kalgren et al. |
| 2002/0082665 A1 | 6/2002 | Haller et al. |
| 2002/0091310 A1 | 7/2002 | Jentsch et al. |
| 2002/0128872 A1 | 9/2002 | Giammattei |
| 2002/0135336 A1 | 9/2002 | Zhou et al. |
| 2002/0151770 A1 | 10/2002 | Noll et al. |
| 2002/0177782 A1 | 11/2002 | Penner |
| 2002/0177884 A1 | 11/2002 | Ahn et al. |
| 2002/0183806 A1 | 12/2002 | Abrahamson et al. |
| 2002/0198740 A1 | 12/2002 | Roman |
| 2003/0045787 A1 | 3/2003 | Schulze |
| 2003/0067736 A1 | 4/2003 | Vahamaki |
| 2003/0069644 A1 | 4/2003 | Kovacevic et al. |
| 2003/0093503 A1 | 5/2003 | Yamaki et al. |
| 2003/0154411 A1 | 8/2003 | Hovik |
| 2003/0172940 A1 | 9/2003 | Rogers et al. |
| 2004/0008123 A1 | 1/2004 | Carrender |
| 2004/0010184 A1 | 1/2004 | Kenknight et al. |
| 2004/0011137 A1 | 1/2004 | Hnat et al. |
| 2004/0011366 A1 | 1/2004 | Schulman et al. |
| 2004/0019384 A1 | 1/2004 | Kirking et al. |
| 2004/0030395 A1 | 2/2004 | Blunn et al. |
| 2004/0073279 A1 | 4/2004 | Malackowski et al. |
| 2004/0078219 A1 | 4/2004 | Kaylor et al. |
| 2004/0113790 A1* | 6/2004 | Hamel et al. ............... 340/572.1 |
| 2004/0138663 A1 | 7/2004 | Kosashvili |
| 2004/0138925 A1 | 7/2004 | Zheng |
| 2004/0171924 A1 | 9/2004 | Mire et al. |
| 2004/0178955 A1 | 9/2004 | Menache et al. |
| 2004/0204744 A1 | 10/2004 | Penner et al. |
| 2004/0230226 A1 | 11/2004 | Bingham |
| 2005/0010299 A1 | 1/2005 | DiSilvestro |
| 2005/0010300 A1 | 1/2005 | Disilvestro et al. |
| 2005/0010301 A1 | 1/2005 | Disilvestro et al. |
| 2005/0010302 A1 | 1/2005 | Dietz et al. |
| 2005/0027330 A1 | 2/2005 | Govari |
| 2005/0055316 A1 | 3/2005 | Williams |
| 2005/0061336 A1 | 3/2005 | Goetz et al. |
| 2005/0065815 A1 | 3/2005 | Mazar |
| 2005/0075697 A1 | 4/2005 | Olson et al. |
| 2005/0091338 A1 | 4/2005 | de la Huerga |
| 2005/0099290 A1 | 5/2005 | Govari |
| 2005/0101962 A1 | 5/2005 | Schwenke |
| 2005/0113887 A1 | 5/2005 | Bauhahn |
| 2005/0119716 A1 | 6/2005 | McClure et al. |
| 2005/0165317 A1 | 7/2005 | Turner et al. |
| 2005/0288739 A1 | 12/2005 | Hassler |
| 2005/0288740 A1 | 12/2005 | Hassler |
| 2005/0288741 A1 | 12/2005 | Hassler |
| 2006/0009856 A1* | 1/2006 | Sherman et al. ........... 623/20.32 |
| 2006/0030945 A1* | 2/2006 | Wright ....................... 623/20.15 |
| 2006/0074319 A1 | 4/2006 | Barnes et al. |
| 2006/0136013 A1* | 6/2006 | Sherman .......................... 607/60 |
| 2006/0190080 A1* | 8/2006 | Danoff et al. .............. 623/17.11 |
| 2007/0005141 A1* | 1/2007 | Sherman ................... 623/18.12 |
| 2007/0179627 A1* | 8/2007 | Gustilo et al. ............. 623/20.15 |
| 2007/0239282 A1* | 10/2007 | Caylor et al. .............. 623/20.34 |
| 2008/0065225 A1 | 3/2008 | Wasielewski et al. |

FOREIGN PATENT DOCUMENTS

| | | |
|---|---|---|
| EP | 1264514 A2 | 12/2002 |
| EP | 1264614 A2 | 12/2002 |
| EP | 1 570 782 A2 | 3/2005 |
| EP | 1 571 581 A1 | 3/2005 |
| EP | 1611835 | 1/2006 |
| EP | 1671577 | 6/2006 |
| GB | 2 239 802 A | 7/1991 |
| GB | 2382777 | 6/2003 |
| WO | 9217113 | 10/1992 |
| WO | 99/56614 A1 | 11/1999 |
| WO | 00/13585 A1 | 3/2000 |
| WO | 0119239 A1 | 3/2001 |
| WO | 01/37926 A1 | 5/2001 |
| WO | 0143823 A1 | 6/2001 |
| WO | 01/49173 A1 | 7/2001 |
| WO | 0148675 A2 | 7/2001 |
| WO | 0169974 A2 | 9/2001 |
| WO | 02/080753 A2 | 10/2002 |
| WO | 02/091399 A1 | 11/2002 |
| WO | 02/094113 A1 | 11/2002 |
| WO | 03066159 A2 | 8/2003 |

| WO | 03077752 A1 | 9/2003 |
| WO | 03095024 A2 | 11/2003 |
| WO | 2004/026399 A1 | 4/2004 |
| WO | 2004028627 A1 | 4/2004 |
| WO | 2004030757 A1 | 4/2004 |
| WO | 2004030759 A1 | 4/2004 |
| WO | 4039256 A2 | 5/2004 |
| WO | 2005/084544 A1 | 9/2005 |
| WO | 2005/120203 A2 | 12/2005 |

OTHER PUBLICATIONS

D'Lima, D.D. Townsend, C.P., Arms, S.W., Morris, B.A., Colwell Jr., C.W., 2005. An implantable telemetry device to measure intra-articulartibial forces. Journal of Biomechanics 38 (299-304).

Graichen, F., Bergmann, G., Rohlmann, A., 1999. Implantable Telemetry System for Measurement of Hip Joint Force and Termperature. 15th Int. Symposium of Biotelemetry, Juneau, Alaska, USA. (Abstract).

Want, "RFID a Key to Automating Everything", Scientific American, Jan. 2004, pp. 56-65 (13 pages).

"Application Note" nRF24E1 and nRF24E2 RF layout nAN24-03 Jun. 2004 (6 pages) Nordic Semiconductor ASA (Revision 2.0).

European Search Report for European Application No. EP05257906.7-2305, Mar. 30, 2006, 6 pages.

National Semiconductor LM62 2.7V, 15.6 mVrC, SOT-23 Temperature Sensor, Jun. 1999 (8 pages) 2001 National Semiconductor Corporation Article.

"Surgeon at Scripps Clinic Implants One-of-a-Kind 'Electronic Knee'—Revolutionizing Research in Knee Implant Technology" (1 pages) Scripps Clinic Oct. 21, 2004 Article.

European Search Report for European Application No. 05257763.2-2305, Mar. 13, 2006, 5 pages.

* cited by examiner

TIBIAL TRAY ASSEMBLY HAVING A WIRELESS COMMUNICATION DEVICE

TECHNICAL FIELD

The present disclosure relates generally to orthopaedic prosthesis, and particularly, to tibial tray assemblies including wireless communication devices.

BACKGROUND

Joint arthroplasty is a well-known surgical procedure by which a diseased and/or damaged natural joint is replaced by a prosthetic joint. A typical orthopaedic prosthesis for the knee includes a tibial tray, a femoral component, and a polymer insert or bearing positioned between the tibial tray and the femoral component. The tibial tray may include a stem or post that is implanted into the surgically prepared proximal end of the tibia to provide stability. In some applications, a stem extension may be coupled to the stem of the tibial tray to increase the overall length of the stem.

SUMMARY

According to one aspect, a tibial tray assembly may include a platform and a stem extending downwardly from a bottom surface of the platform. The platform may include an upper surface configured to receive a tibial insert. The tibial tray assembly may also include a stem extension coupleable to an end of the stem. The stem extension may be electrically insulated from the stem. For example, the tibial tray assembly may include an electrical insulator coupleable to the stem and the stem extension. The electrical insulator may be configured to be positioned between the stem and the stem extension when coupled thereto. The electrical insulator may be formed from a polyethylene material. The stem and the stem extension may be formed from the same material. The stem extension may be tuned to a quarter-wavelength of 2,450 Megahertz. For example, the stem extension may have a length of about 1.2 inches.

The tibial tray assembly may further include a wireless communication device. The wireless communication device may be configured to transmit data using the stem extension as an antenna. The wireless communication device may be configured to transmit the data at a frequency of about 2,450 Megahertz using the stem extension as an antenna. Additionally or alternatively, the wireless communication device may be configured to transmit the data a distance less than about ten feet at a signal level of about −90 dBm. The wireless communication device may be positioned in an internal cavity of the stem. In some embodiments, the wireless communication device may be configured to transmit the data in response to receipt of an interrogation signal. The wireless communication device may include, for example, a transmitter or transceiver and a sensor coupled to the transmitter. The transmitter/transceiver may be configured to transmit data generated by the sensor.

According to another aspect, an orthopaedic prosthesis may include a tibial tray, a spacer, a stem extension, and a wireless communication device. The tibial tray may include a platform and a stem extending downwardly from a bottom surface of the platform. The spacer may be coupleable to an end of the stem of the tibial tray. The spacer may be formed from an electrically insulative material. Additionally, the spacer may include a first threaded bore on a first end and a second threaded bore on a second end. The stem extension may be coupleable to the first stem extension. The stem extension may be tuned to a quarter-wavelength of 2,450 Megahertz. For example, the stem extension may have a length of about 1.2 inches. The wireless communication device may be configured to transmit data using the stem extension as an antenna. For example, the wireless communication device may be configured to transmit the data at a frequency of about 2,450 Megahertz using the stem extension as an antenna.

Additionally or alternatively, the wireless communication device may be configured to transmit the data a distance less than about ten feet at a signal level of about −90 dBm. In some embodiments, the wireless communication device may be configured to transmit the data in response to receipt of an interrogation signal. The wireless communication device may include, for example, a transmitter or transceiver and a sensor coupled to the transmitter. The transmitter/transceiver may be configured to transmit data generated by the sensor.

According to yet another aspect, a tibial tray assembly may include a platform and a stem extending downwardly from a bottom surface of the platform. The platform may include an upper surface configured to receive a tibial insert. The tibial tray assembly may also include a stem extension coupled to an end of the stem. The tibial tray assembly may further include a spacer coupled between the stem and the stem extension. The spacer may electrically insulate the stem extension from the stem. The tibial tray may also include a wireless communication device. The wireless communication device may be positioned in the stem and electrically coupled to the stem extension, the wireless communication device configured to transmit data using the stem extension as an antenna.

BRIEF DESCRIPTION OF THE DRAWINGS

The detailed description particularly refers to the following figures, in which.

DETAILED DESCRIPTION OF THE DRAWINGS

Figure 1:
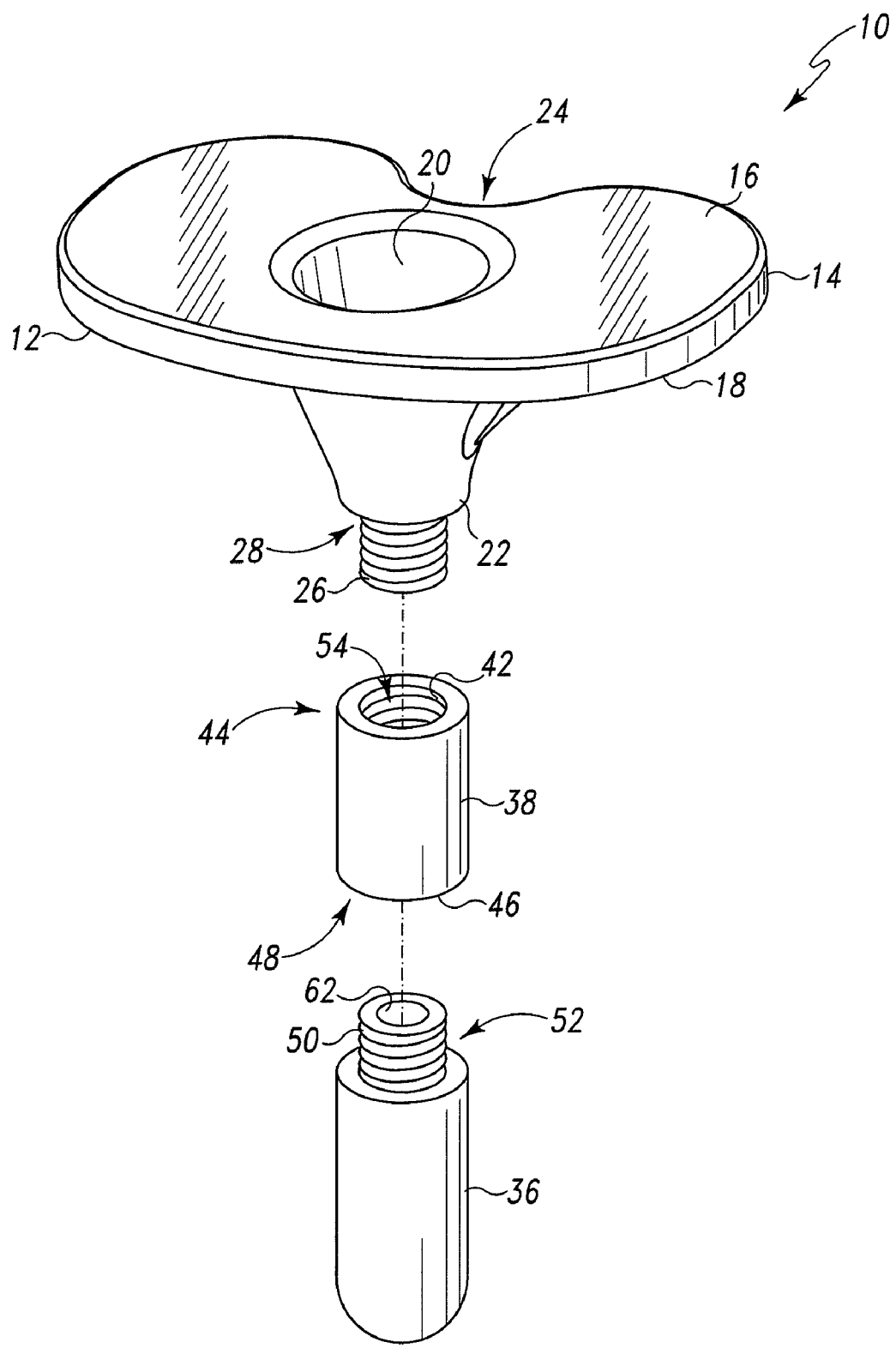
FIG. 1 is an exploded perspective view of one embodiment of an orthopaedic prosthesis having a wireless communication device.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring to FIG. 1, a tibial tray assembly 10 includes a tibial tray 12 having a platform 14. The platform 14 includes an upper surface 16 and a bottom surface 18. The upper surface 16 of the platform 14 is configured to receive a tibial bearing or insert (not shown). Illustratively, the tibial tray 12 is configured for use with a mobile tibial bearing. As such, the tibial tray 12 includes an aperture 20 defined in the upper surface 16 of the platform 14. The aperture 20 is configured to receive a stem of the mobile tibial bearing. In use, the tibial bearing may be configured to rotate about an axis defined by the stem of the bearing or otherwise rotate, slide, or move in one or more directions. However, in other embodiments, the tibial tray 12 may be configured for use with or be otherwise usable with a fixed tibial bearings. In such embodiments, the tibial tray 12 may or may not include the aperture 20. As such, the tibial tray 12 may include additional features in other embodiments such as, for example, a track, slot, or other feature in or on the platform 12 based on the particular application and/or type of tibial bearing to be used. Accordingly, although the tibial tray 12 is illustrated in and described below in regard to use with a mobile tibial bearing, it should be appreciated that the tibial tray 12 may be used with and/or modified for use with a fixed tibial bearing in other embodiments.

The tibial tray 12 is configured to be coupled to a surgically-prepared surface of the proximal end of a patient's tibia as illustrated in and discussed in more detail below in regard to FIG. 5. The tibial tray 12 includes a stem 22 extending downwardly from the bottom surface 18 of the platform 14. When the tibial tray 12 is coupled to the patient's tibia, the stem 22 is embedded in the patient's tibia to thereby secure the tibial tray 12 to the patient's bone.

The platform 14 has a generally oval top profile. In some embodiments, may include an inwardly curving wall portion 24 such that the top profile of the platform 14 generally corresponds to the shape of the surgically-prepared surface of the proximal end of the patient's tibia. However, the platform 14 may have other configurations in other embodiments.

Figure 2:
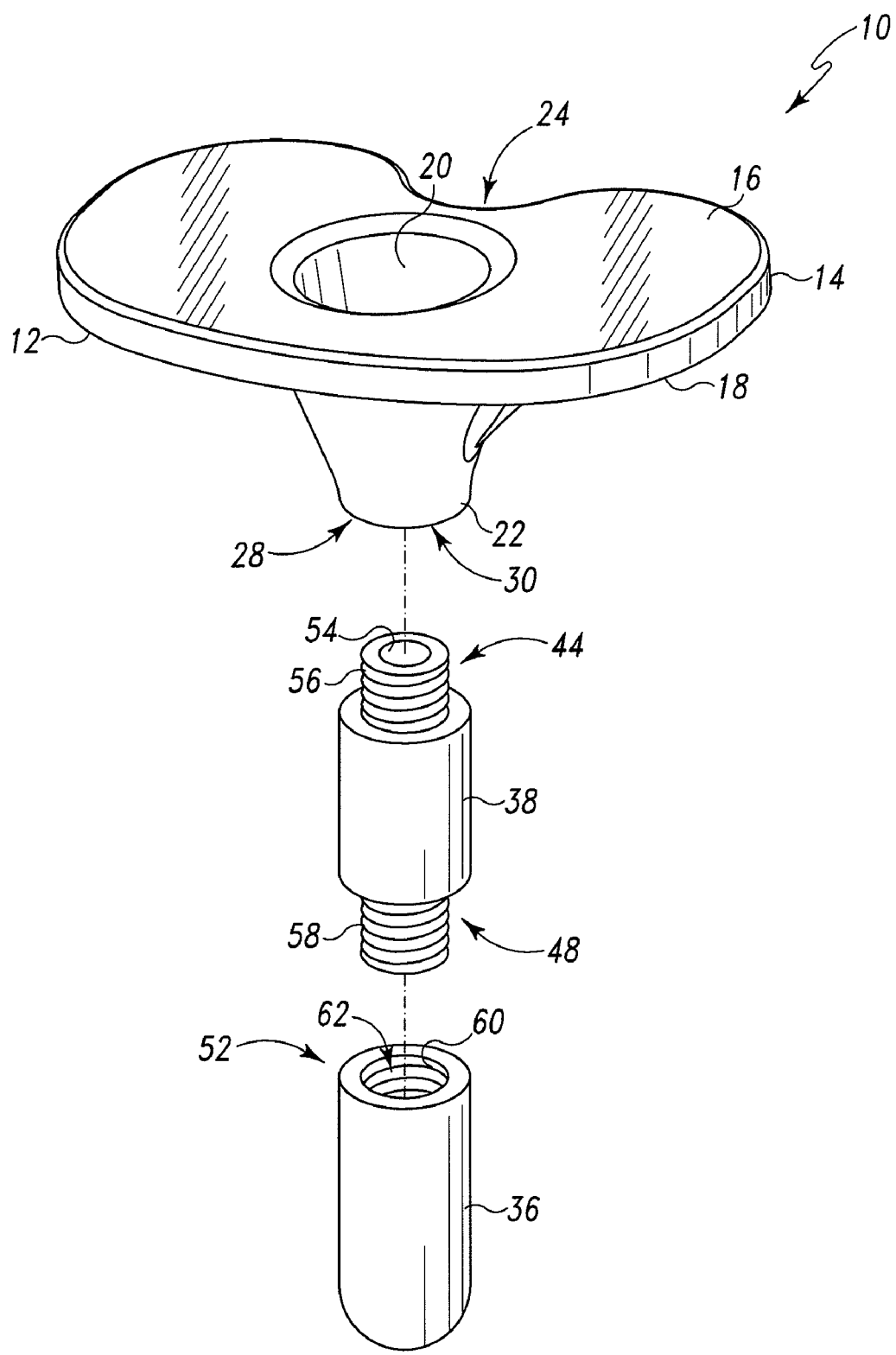
FIG. 2 is an exploded perspective view of another embodiment of the orthopaedic prosthesis of FIG. 1.

The stem 22 may extend downwardly from the bottom surface 18 of the platform 14 any distance. In some embodiments, the stem 22 includes a threaded stud 26 located at the distal end 28 of the stem 22 as illustrated in FIG. 1. However, in other embodiments, the stem 22 may include a threaded bore 30 defined in the distal end 28 of the stem 22 as illustrated in FIG. 2. The stem 22 includes an internal passageway 32 (see FIG. 3) having an open end at the distal end 28 of the stem 22. As discussed in more detail below in regard to FIG. 3, the internal passageway 32 is configured to house an antenna wire, which extends out of the stem 22. Additionally, in some embodiments, the stem 22 and/or platform 14 may include an internal chamber 34 (see FIG. 3) defined therein for housing electrical devices such as wireless communication devices.

Figure 3:
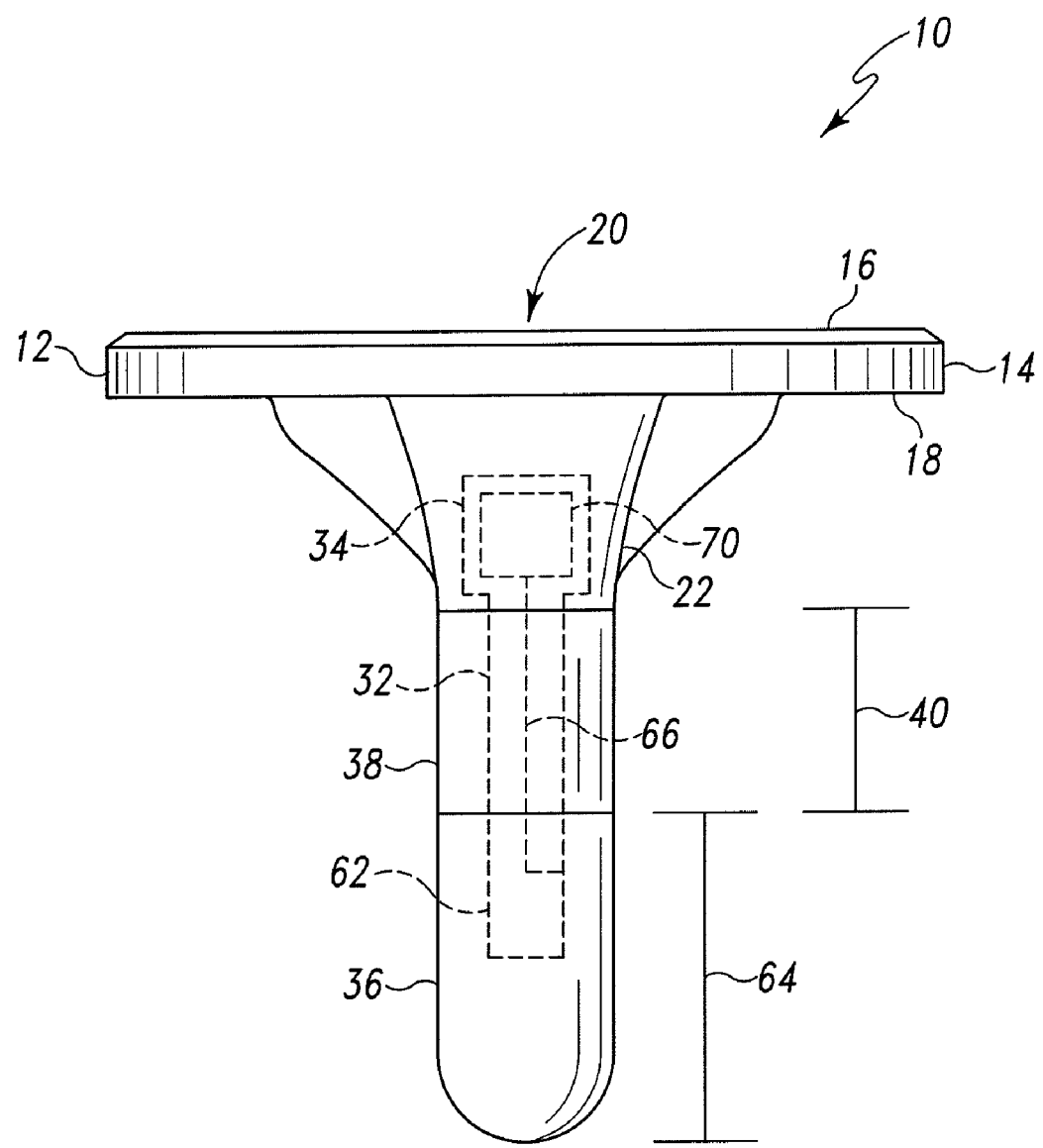
FIG. 3 is a side elevation view of the orthopaedic prosthesis of FIG. 1 in an assembled configuration.

The tibial tray assembly 10 also includes a stem extension 36 and an insulative stem spacer or extension 38. The spacer 38 is configured to be coupled to the distal end 28 of the stem 22 of the tibial tray 12. Similarly, the stem extension 36 is configured to be coupled to a distal end 40 of the spacer 38. As illustrated in FIG. 3, when the tibial tray 12, the spacer 38, and the stem extension 36 are coupled together, the spacer 38 is positioned between the stem extension 36 and the stem 22 of the tibial tray 12. The spacer 38 is formed from an electrically insulative material such as, for example, a polyethylene material. Because the spacer 38 is formed from an insulative material, the spacer 38 forms an electrical insulator between the stem extension 36 and the stem 22 of the tibial tray 12 when the tibial tray assembly 10 is assembled as illustrated in FIG. 3.

In the illustrative embodiment of FIGS. 1-4, the spacer 38 has a substantially cylindrical shape and body length 40 of about 0.5 inches (see FIG. 3). However, in other embodiments, spacers 38 having different shapes and sizes may be used. That is, the spacer 38 may have any configuration that allows the spacer 38 to be coupled to the stem 22 and the stem extension 36 and provide electrical insulation therebetween. For example, in other embodiments, the spacer 38 may be embodied as an insulative washer, nut, or the like. Additionally, although the spacer 38 is illustrated in FIGS. 1 and 2 as removably coupleable to the stem extension 36, the spacer 38 may be secured to the stem extension 36 in some embodiments. For example, the spacer 38 may be secured to the stem extension 36 via a suitable adhesive or the like.

In embodiments wherein the stem 22 of the tibial tray 12 includes a threaded stud 26 as illustrated in FIG. 1, the spacer 38 includes a threaded bore 42 defined in a proximal end 44 of the spacer 38. The threaded bore 42 is configured to receive the threaded stud 26 when the spacer 38 is coupled to the stem 22 of the tibial tray 12 (i.e., when the spacer 38 is screwed onto the threaded stud 26). The spacer 38 also includes a threaded bore 46 defined in a distal end 48 of the spacer 38. In such embodiments, the threaded bore 42 is configured to receive a threaded stud 50 defined on a proximal end 52 of the stem extension 36. Additionally, the spacer 38 includes an internal passageway 54 (see, e.g., FIG. 3) having open ends at each end 44, 48 of the spacer. Again, as discussed in more detail below in regard to FIG. 3, the internal passageway 54 is configured to house an antenna wire, which extends through the spacer 38.

Conversely, in embodiments wherein the stem 22 of the tibial tray 12 includes a threaded bore 30 as illustrated in FIG. 2, the spacer 38 includes a threaded stud 56 defined on the proximal end 44 of the spacer 38. The threaded stud 56 is configured to be received by the treaded bore 30 when the spacer 38 is coupled to the stem 22 of the tibial tray 12 (i.e., when the spacer 38 is screwed into the threaded bore 30). The spacer 38 also includes a threaded stud 58 defined on the distal end 48 of the spacer 38. In such embodiments, the threaded stud 58 is configured to be received by a threaded bore 60 defined in the proximal end 52 of the stem extension 36.

As such, it should be appreciated that the stem 22, the spacer 38, and the stem extension 36 may have any one of a number of configurations to facilitate the coupling therebetween. Although in the illustrative embodiments, the stem 22 and extensions 36, 38 are configured to be coupled together via threaded bores and studs, the stem 22 and extensions 36, 38 may be coupled together using other devices and/or means in other embodiments. For example, in some embodiments, the stem 22, the spacer 38, and/or the stem extension 36 may include one or more tapered joints configured to be coupled together to thereby secure the stem 22 and the extensions 36, 38 together. Additionally, in other embodiments, the stem 22 and extensions 36, 38 may be configured to be coupled together via use of one of a number of securing devices such as, for example, an adhesive. As such, the stem 22 and extensions 36, 38 may be coupled to each other using any one of a number of methods and/or securing devices such that the spacer 38 is electrically insulated from the stem 22.

As discussed in more detail below in regard to FIGS. 3 and 4, the stem extension 36 is configured for use as an antenna (e.g., a half-dipole antenna). As such, the stem extension 36 is formed from a metallic material such as, for example, a titanium alloy. In some embodiments, the stem extension 36 is formed from the same material as the tibial tray 12. The stem extension 36 may include an internal passageway 62 for housing the antenna wire 66 in some embodiments as illustrated in FIG. 3. Additionally, to facilitate the use of the stem extension 36 as an antenna, the stem extension 36 may be tuned to a particular frequency and/or wavelength of a particular frequency. To do so, the length 64 of the stem extension 36 may be determined based on the particular frequency. For example, in one particular embodiment, the stem extension 36 is tuned to the quarter-wavelength of 2,450 Megahertz. That is, the stem extension 36 may have a length 64 tuned to the quarter-wavelength of 2,450 Megahertz. As such, the stem extension 36 may have a length 64 of about 2.4 inches. However, in other embodiments, the stem extension 36 having other lengths may be used to facilitate wireless communication using any one of a number of frequencies. Additionally, although the illustrative stem extension 36 has a substantially cylindrical shape, stem extensions having other shapes and sizes may be used in other applications based on the particular implementation such as age of the patient, transmission frequency used, and the like.

Referring now to FIG. 3, the tibial tray assembly 10 also includes a wireless communication device 70. In some embodiments, the wireless communication device 70 may be positioned in the internal chamber 34 of the stem 22 of the tibial tray 12 as illustrated in FIG. 3. However, in other embodiments, the wireless communication device 70 may be positioned in a different location in the tibial tray assembly 10 or otherwise coupled thereto. For example, in some embodiments, the wireless communication device 70 may be positioned in the spacer 38. Additionally, in other embodiments, the wireless communication device may be positioned in or otherwise coupled to the platform 14 of the tibial tray 12.

The wireless communication device 70 is configured to use the stem extension 36 as an antenna. As such, the wireless communication device 70 is electrically coupled to the stem extension 36 via the antenna wire 66. As illustrated in FIG. 3, the antenna wire 66 extends from the wireless communication device 70, through the internal passageway 32 of the spacer 38, and is electrically coupled to the stem extension 36 (e.g., in the internal passageway 62 of the stem extension 36). The antenna wire 66 may be embodied as any type of electrically shielded communication wire or link such as number of wires, cables, or the like.

Figure 4:
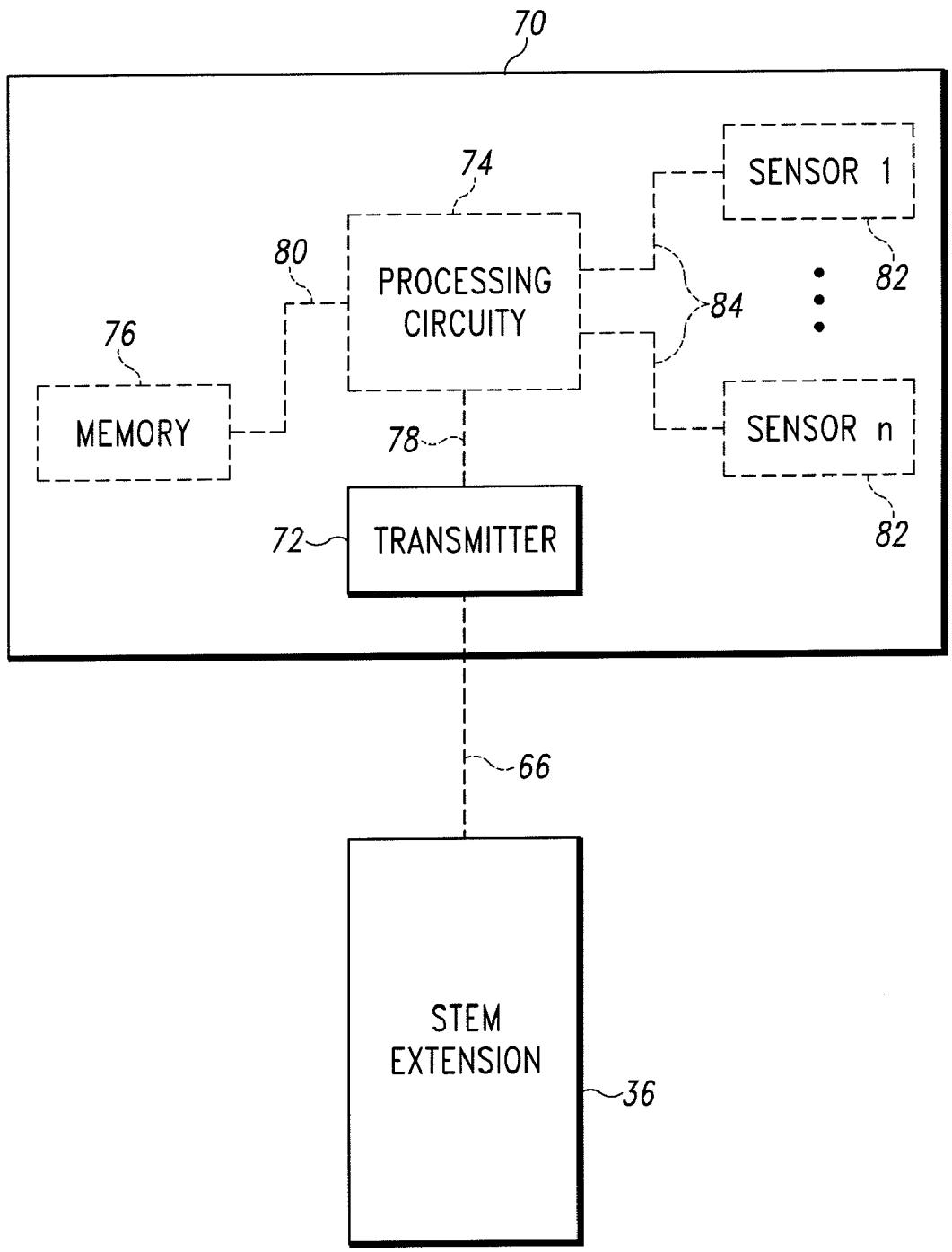
FIG. 4 is block diagram of one embodiment of a wireless communication device of the orthopaedic prostheses of FIGS. 1 and 2.

Referring now to FIG. 4, the wireless communication device 70 includes a transmitter or transceiver circuit 72. The transmitter circuit 72 is electrically coupled to the stem extension 36 via the antenna wire 66. The transmitter circuit 72 is configured to transmit data using the stem extension 36 as an antenna. As such, the transmitter circuit 72 and/or the wireless communication device 70 may include additional circuitry and/or devices to facilitate the transmission of such data. For example, in some embodiments, the wireless communication device 70 may include processing circuitry 74 and a memory device 76. The processing circuitry 74 may be embodied as any type of processing circuitry including, for example, discrete processing circuitry (e.g., a collection of logic devices), general purpose integrated circuit(s), and/or application specific integrated circuit(s) (i.e., ASICs). The memory device 76 may be embodied as any type of memory device and may include one or more memory types, such as, random access memory (i.e., RAM) and/or read-only memory (i.e., ROM). In addition, the wireless communication device 70 may include other devices and circuitry typically found in a wireless communication circuit for performing the functions described herein such as, for example, a power source circuit, a crystal, a timing circuit, and the like.

In those embodiments including the processing circuitry 74 and the memory device 76, the processing circuitry 74 is electrically coupled to the transmitter 72 via a communication link 78 and to the memory device 76 via a communication link 80. The communication links 78, 80 may be embodied as any type of communication links capable of facilitating electrical communication between the processing circuitry 74, the memory device 76, and the transmitter 72. For example, the communication links 78, 80 may be embodied as any number of wires, cables, printed circuit board traces, vias, and/or the like.

Additionally, in some embodiments, the wireless communication device 70 may include a number of sensors 82. The sensors 82 may be embodied as any type of sensors including, for example, temperature sensors, pressure sensors, load sensors, strain sensors, and/or the like. The sensors 82 may be housed in the tibial tray assembly 10, coupled to the assembly 10 (e.g., coupled to the platform 14 of the tibial tray 12), or remote therefrom. The sensors 82 are electrically coupled to the processing circuitry 74 via a number of communication links 84. The communication links 84 may be embodied as any type of communication links capable of facilitating electrical communication between the processing circuitry 74 and the sensors 82. For example, as with the communication links 78, 80, the communication links 84 may be embodied as any number of wires, cables, printed circuit board traces, vias, and/or the like.

In some embodiments, the processing circuitry 74 may be configured to retrieve data from the memory device 76 and transmit the data via use of the transmitter 72 and the stem extension 36. Such data may be embodied as any type of data including, but not limited to, product identification data, patient-related data, and/or the like. Additionally, in embodiments including the sensors 82, the processing circuitry 74 may be configured to receive sensor data form the sensors 82 and transmit the sensor data using the transmitter 72 and the stem extension 36 as an antenna. Additionally or alternatively, the processing circuitry 74 may be configured to store the sensor data in the memory device 76.

In some embodiments, the wireless communication device 70 is configured to transmit the data (e.g., data retrieved from the memory device 76 or received form the sensors 82) in response to a received interrogation signal. That is, the processing circuitry 74 may be configured to not transmit data unless the interrogation signal has been received. In this way, privacy of the data is increased because the wireless communication device 70 is not continually transmitting data. Additionally, in some embodiments, the wireless communication device 70 and/or the stem extension 36 are configured such that the range of wireless communication is restricted to a defined distance. To do so, the signal power of the wireless communication device 70 and/or the antenna gain of the stem extension 36 may be selected to generate a predetermined range of operation. For example, typical receiver devices have a minimum discernable signal level of about −90 dBm. As such, the wireless communication device 70 and/or the stem extension 36 may be configured to generate a signal having a signal level of about −90 dBm or less at a predetermined distance form the tibial tray assembly. For example, in one particular embodiment, the wireless communication device 70 and/or the stem extension 36 are configured to generate a signal having a signal level of about −90 dBm or less at a distance of about ten feet from the tibial tray assembly. In this way, the privacy of the data is increased because the range of reception of the signal transmitted by the wireless communication device 70 is restricted.

Figure 5:
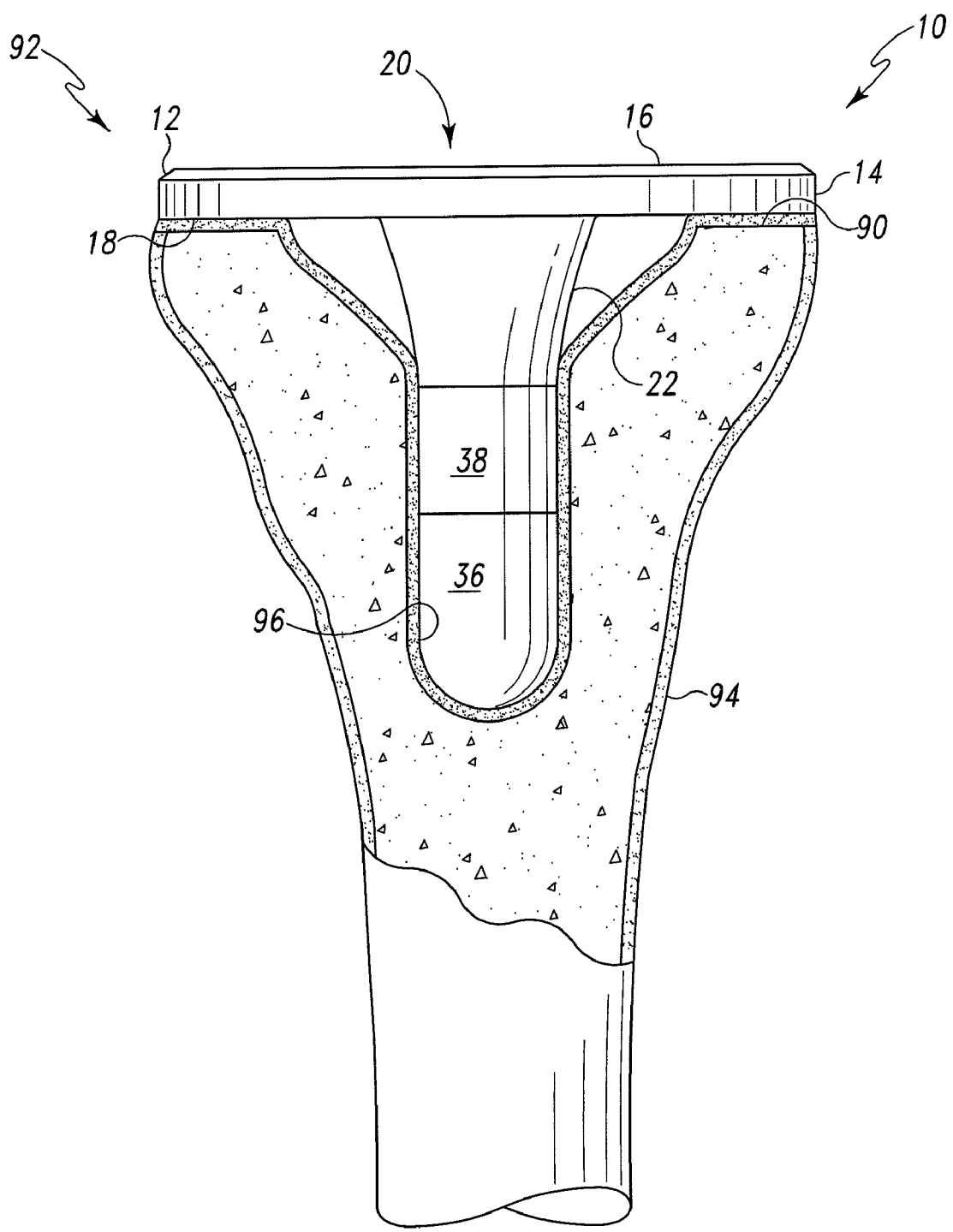
FIG. 5 is cross-sectional view of the orthopaedic prosthesis of FIG. 1 secured to a bone of a patient.

Referring now to FIG. 5, the tibial tray assembly 10 is configured to be coupled to a surgically-prepared surface 90 of the proximal end 92 of a patient's tibia 94. When the tibial tray assembly 10 is coupled to the patient's tibia 94, the stem 22, spacer 38, and stem extension 36 are embedded in the patient's tibia 94 to thereby secure the tibial tray assembly 10 to the patient's bone. In one embodiment, the tibial tray assembly 10 may be secured to the patient's tibia 94 via use of bone cement 96. The bone cement 96 forms a barrier around the stem extension 36 thereby insulating the stem extension 36 from any conductive tissue or fluids. The spacer 38 also insulates the stem extension 36 from tibial tray 12, which in the presence of electrically conductive tissues and/or fluids may act as a ground plane to the stem extension 36 during transmission.

Figure 6:
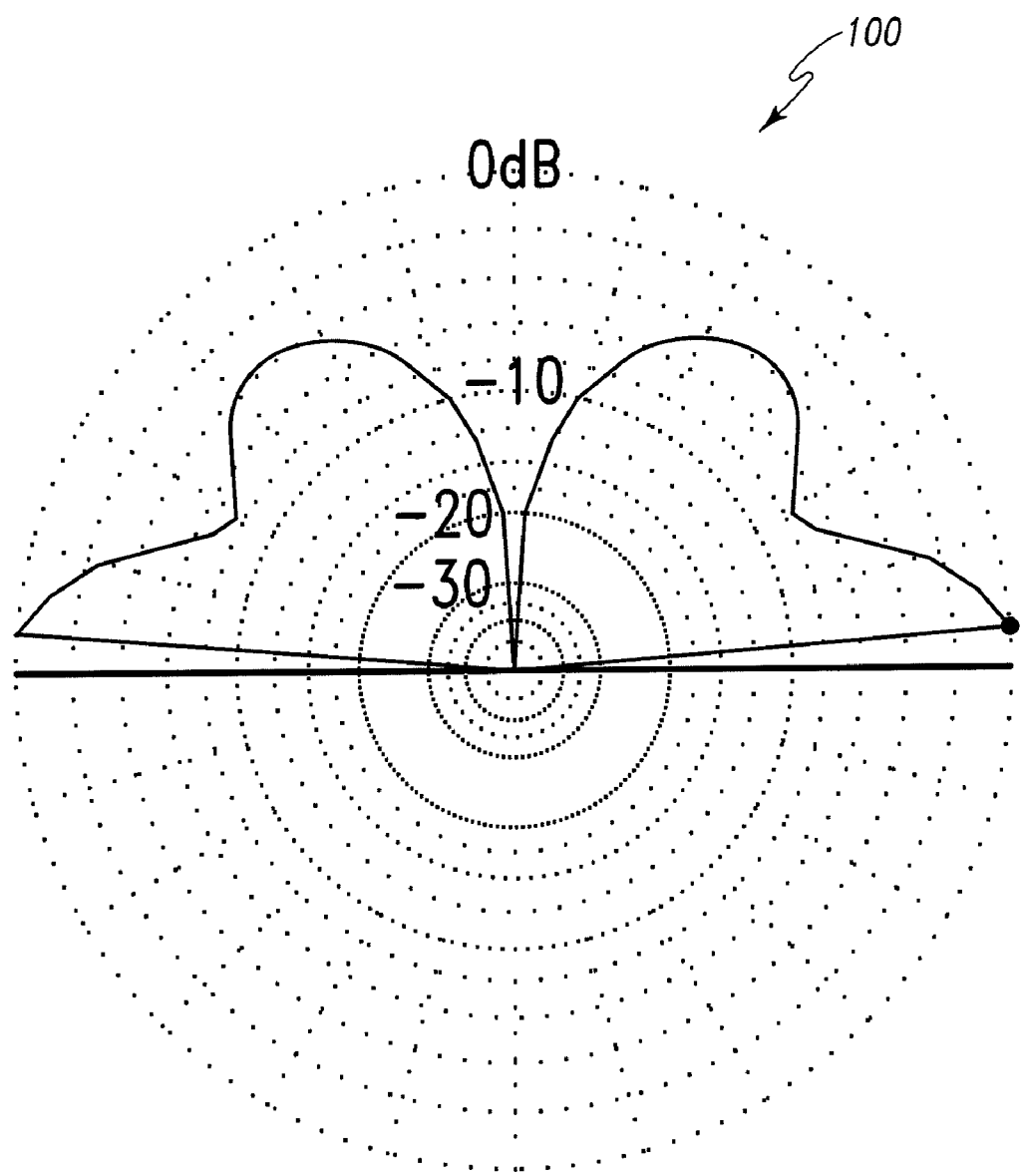
FIG. 6 is an illustrative antenna radiation elevation plot of one embodiment of the wireless communication device of the orthopaedic implant of FIG. 1.
Figure 7:
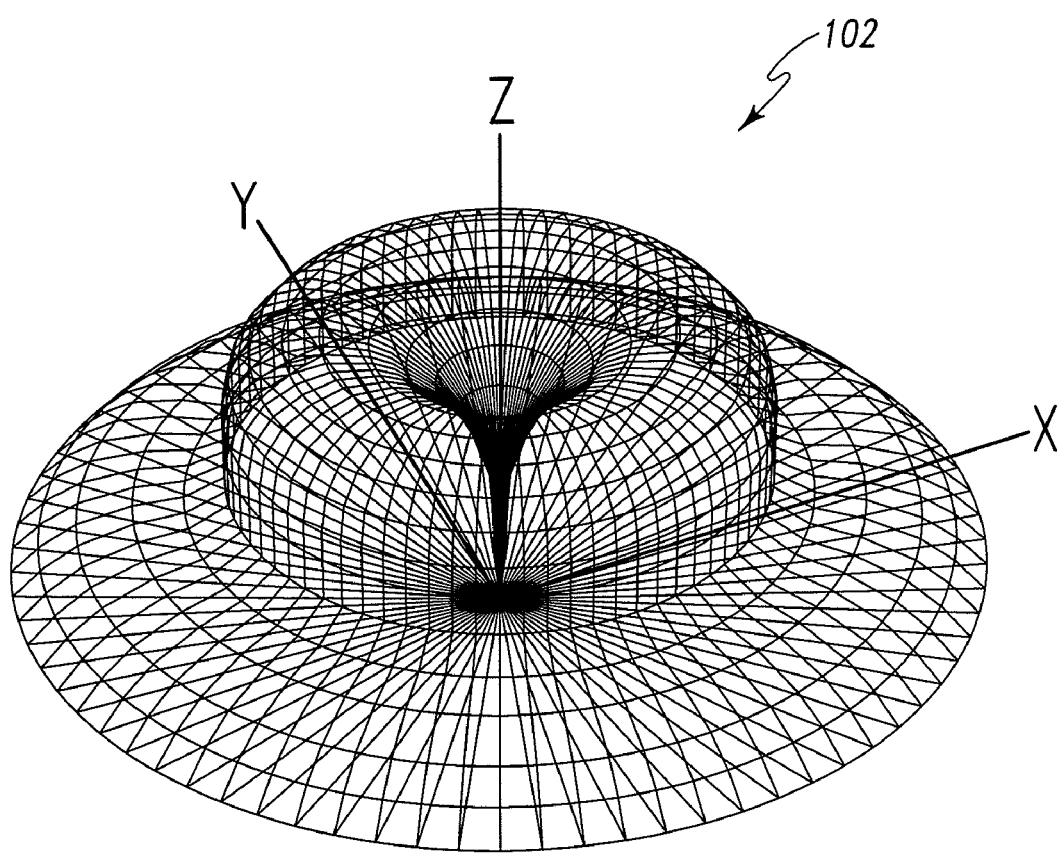
FIG. 7 is another illustrative antenna radiation three-dimensional plot of one embodiment of the wireless communication device of the orthopaedic implant of FIG. 1.

Referring now to FIGS. 6 and 7, an antenna radiation elevation plot 100 and an antenna radiation three-dimensional plot 102 are illustrated. The plots 100, 102 were generated based on a software model of the tibial tray assembly 10, which was modeled using a NEC-3 method of moments based software package. The plots 100, 102 illustrate a typical half-dipole antenna pattern with the tibial tray 12 acting as a ground plane. The take-off angle of the signal generated by the tibial tray assembly 10 was approximately 5 degrees elevation, with a maximum signal gain at the elevation of 10.1 dBi. The antenna pattern is consistent in azimuth, and the average gain across elevation is approximately 3 dBi. Continuous wave signal transmission was verified using the spacer 38 as an antenna and coupled to an RF signal generator in 360 azimuth and 90 elevation cuts.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected. For example, although specific measurement values and ranges and specific frequency values and ranges have been disclosed in various embodiments, it should be appreciated that measurements and/or frequencies near such values may be in used in other embodiments.

There are a plurality of advantages of the present disclosure arising from the various features of the systems and methods described herein. It will be noted that alternative embodiments of the assemblies and devices of the present disclosure may not include all of the features described yet still benefit from at least some of the advantages of such features. Those of ordinary skill in the art may readily devise their own implementations of the assemblies and devices that incorporate one or more of the features of the present invention and fall within the spirit and scope of the present disclosure as defined by the appended claims.

The invention claimed is:

1. A tibial tray assembly comprising:
   a platform having an upper surface configured to receive a tibial insert;
   a stem extending downwardly from a bottom surface of the platform, the stem having a distal end and an internal cavity;
   a spacer having an internal passageway, a proximal end and a distal end, the proximal end of the spacer being secured to the distal end of the stem;
   a stem extension having a metallic body secured to the distal end of the spacer such that (i) the spacer is positioned between the stem and the stem extension, and (ii) the stem extension is physically and electrically insulated from the stem by the spacer;
   a wireless communication device positioned in the internal cavity of the stem, wherein the wireless communication device is electrically coupled to the metallic body of the stem extension and configured to transmit data using the metallic body of the stem extension as an antenna; and
   an antenna wire electrically coupling the wireless communication device to the metallic body of the stem extension, the antenna wire extending through the internal passageway of the spacer.

2. The tibial tray assembly of claim 1, wherein the spacer is formed from a polyethylene material.

3. The tibial tray assembly of claim 1, wherein the stem and the stem extension are formed from the same material.

4. The tibial tray assembly of claim 1, wherein the stem extension is tuned to a quarter-wavelength of 2,450 Megahertz.

5. The tibial tray assembly of claim 1, wherein the metallic body of the stem extension has a length of about 1.2 inches.

6. The tibial tray assembly of claim 1, wherein the wireless communication device is configured to transmit the data at a frequency of about 2,450 Megahertz using the metallic body of the stem extension as an antenna.

7. The tibial tray assembly of claim 1, wherein the wireless communication device is configured to transmit the data a distance less than about ten feet at a signal level of about −90 dBm.

8. The tibial tray assembly of claim 1, wherein the wireless communication device is configured to transmit the data in response to receipt of an interrogation signal.

9. The tibial tray assembly of claim 1, wherein the wireless communication device comprises a transmitter and a sensor coupled to the transmitter, the transmitter being configured to transmit data generated by the sensor.

10. An orthopaedic prosthesis comprising:
    a tibial tray having a platform and a stem extending downwardly from a bottom surface of the platform, the stem having a distal end;
    a spacer having a proximal end coupled to the distal end of the stem of the tibial tray, the spacer being formed from an electrically insulative material, the spacer having a threaded distal end;
    a stem extension having a metallic body and including a threaded proximal end, the threaded proximal end of the stem extension being removably coupled to threaded distal end of the spacer; and
    a wireless communication device having an antenna wire electrically coupled only to the stem extension, the wireless communication device configured to transmit data using only the metallic body of the stem extension as an antenna.

11. The orthopaedic prosthesis of claim 10, wherein the stem extension is tuned to a quarter wavelength of 2,450 Megahertz.

12. The orthopaedic prosthesis of claim 10, wherein the metallic body of the stem extension has a length of about 1.2 inches.

13. The orthopaedic prosthesis of claim 10, wherein the wireless communication device is configured to transmit the data at a frequency of about 2,450 Megahertz using the metallic body of the stem extension as an antenna.

14. The orthopaedic prosthesis of claim 10, wherein the wireless communication device is configured to transmit the data a distance less than about ten feet at a signal level of about −90 dBm.

15. The orthopaedic prosthesis of claim 10, wherein the wireless communication device is configured to transmit the data in response to receipt of an interrogation signal.

16. The orthopaedic prosthesis of claim 10, wherein the wireless communication device comprises a transmitter and a sensor coupled to the transmitter, the transmitter being configured to transmit data generated by the sensor.

17. The orthopaedic prosthesis of claim 10, wherein the spacer includes a first threaded bore on the proximal end and a second threaded bore the distal end.

18. A tibial tray assembly comprising:
- a platform having an upper surface configured to receive a tibial insert;
- a stem extending downwardly from a bottom surface of the platform, wherein the stem includes an internal cavity;
- a spacer having a proximal end coupled to an end of the stem, wherein the spacer includes an internal passageway;
- a stem extension coupled to a distal end of the spacer, the spacer physically and electrically insulating the stem extension from the stem;
- a wireless communication device positioned in the internal cavity of the stem and electrically coupled to the stem extension, the wireless communication device configured to transmit data using the stem extension as an antenna,
- wherein the stem extension has a length selected such that the stem extension is tuned to transmit data at a predetermined frequency; and
- an antenna wire electrically coupling the wireless communication device to the stem extension, the antenna wire extending through the internal passageway of the spacer.

\* \* \* \* \*